US00PP32583P2

(12) United States Plant Patent
Hannink

(10) Patent No.: US PP32,583 P2
(45) Date of Patent: Dec. 8, 2020

(54) ***CLEMATIS* PLANT NAMED 'UTOP013'**

(50) Latin Name: ***Clematis* L.**
Varietal Denomination: UTOP013

(71) Applicant: Patent Hannink BV, Waalwijk (NL)

(72) Inventor: Ton Hannink, Waalwijk (NL)

(73) Assignee: Patent Hannink BV, Waalwijk (NL)

( * ) Notice: Subject to any disclaimer, the term of this patent is extended or adjusted under 35 U.S.C. 154(b) by 0 days.

(21) Appl. No.: 16/602,081

(22) Filed: Aug. 1, 2019

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./226, 228
See application file for complete search history.

*Primary Examiner* — Susan McCormick Ewoldt
*Assistant Examiner* — Karen M Redden
(74) *Attorney, Agent, or Firm* — Weatherly IP Solutions, LLC; Barbara Campbell

(57) ABSTRACT

A new *Clematis* plant particularly distinguished by light violet, medium to large flower diameter; and early to medium flowering, first flowers in May/June and flowers again in early Autumn, is disclosed.

1 Drawing Sheet

Genus and species: *Clematis* L.
Variety denomination: 'UTOP013'.

BACKGROUND OF THE NEW PLANT

The present invention comprises a new and distinct variety of *Clematis*, botanically known as *Clematis* L. and hereinafter referred to by the variety name 'UTOP013'. 'UTOP013' originated from a controlled cross in April 2014 in Drunen, The Netherlands between the female parent, *Clematis* 'Utopia' (unpatented) and the male parent *Clematis courtoisii* (unpatented).

Seeds from the controlled cross were obtained and sown and plants were grown for evaluation. A single plant was selected in May 2012 in Drunen, The Netherlands and subsequently named 'UTOP013'. In June 2014 'UTOP013' was first vegetatively propagated in Drunen, The Netherlands by vegetative stem cuttings. 'UTOP013' was found to reproduce true to type in successive generations of sexual propagation via vegetative cuttings in Drunen, The Netherlands.

SUMMARY

The following are the most outstanding and distinguishing characteristics of this new variety when grown under normal horticultural practices in Drunen, The Netherlands.

1. Light violet, medium to large flower diameter; and
2. Early to medium flowering, first flowers in May/June and flowers again in early Autumn.

DESCRIPTION OF THE PHOTOGRAPH

This new *Clematis* plant is illustrated by the accompanying photograph which shows the individual parts of the plant. The photograph is of an approximately two years plant grown in Drunen, The Netherlands, under greenhouse conditions, in April 2014 Drunen, The Netherlands. The colors shown are as true as can be reasonably obtained by conventional photographic procedures. From left to right, the top row shows the upper surface of two petals, the lower surface of two petals; from left to right, the second row shows the lower surface of an individual flower, the flower bud and pedicel, and the upper surface of an immature compound leaf; and the third row shows the upper surface of the flower and the upper surface of a mature compound leaf.

DESCRIPTION OF THE NEW VARIETY

The following detailed descriptions set forth the distinctive characteristics of 'UTOP013'. The data which define these characteristics were collected from asexual reproductions carried out in Drunen, The Netherlands. Data was collected on two years plants in a greenhouse in April 2014. Color references are to The R.H.S. Colour Chart of The Royal Horticultural Society of London (R.H.S.), 5$^{th}$ edition (2007).

Classification:
- *Family*.—Ranunuculaceae.
- *Botanical*.—*Clematis* L.
- *Common*.—*Clematis*.
- *Designation*.—'UTOP013'.

Parentage:
- *Female parent*.—*Clematis* 'Utopia'.
- *Male parent*.—*Clematis courtoisii*.

Plant:
- *Type*.—Climbing.
- *Vigor*.—Weak to medium.
- *Young shoot, presence of pubescence*.—Present and medium to dense.
- *Habit of flowering*.—On both previous year's and current year's growth.
- *Time of beginning of flowering*.—Early to medium, first flowers in May/June.
- *Hardiness/cold tolerance*.—−10 degrees Celsius under "dry" conditions.
- *Stem*.—Number of stems per plant: 2 to 10. Length of stem: 2.0 meters. Diameter of stem: 2.0 mm to 8.0 mm. Stem color: Brown, RHS 153D. Stem texture and appearance: Smooth and round.

Foliage:

*Type*.—Ternate and compound.

*Leaf length*.—8.0 cm to 10.0 cm.

*Leaf width*.—6.0 cm to 10.0 cm.

*Leaflet length*.—7.0 cm to 9.5 cm.

*Leaflet width*.—3.0 cm to 4.5 cm. Shape: Lanceolate. Apex: Acuminate. Base: Rounded. Margin: Entire. Lobing: Present; 3 or 4 lobes; medium depth of sinus between lobes. Color of upper surface of leaf: Medium-green, RHS 137B. Variegation: Absent. Rugosity of upper surface of leaf: Moderate. Texture (both upper and lower surfaces): Smooth.

*Petiole*.—Length: 6.0 cm to 8.0 cm. Diameter: 1.0 mm to 2.0 mm. Texture: Smooth. Color: RHS 153D.

*Petiolule*.—Length: 3.0 cm to 4.0 cm. Diameter: 0.5 mm to 1.0 mm. Texture: Smooth. Color: RHS 153D.

Flowers:

*Arrangement*.—Solitary.

*Flower bud*.—Shape: Cone-shaped. Length: 13.0 mm to 21 mm. Diameter: 8.0 mm to 12.0 mm. Color: RHS 60A and RHS 137D.

*Length of pedicel*.—Short to medium, 13.0 mm to 21.0 mm.

*Pedicel diameter*.—1.0 mm to 2.0 mm.

*Pedicel color*.—RHS 153D.

*Average number of flowers per plant*.—20 to 100 depending on the age of the plant.

*Lastingness of the blooms*.—About 14 days.

*Flower attitude*.—Upwards.

*Flower type*.—Single.

*Flower diameter*.—Medium to large, 12 cm to 14 cm.

*Flower shape*.—Rotate.

*Flower cross-section, lateral view*.—Concave.

*Flower fragrance*.—Absent or very weak.

*Tepal quantity*.—6.

*Tepal arrangement*.—Touching.

*Tepal length*.—Medium to long, 4.0 cm to 7.0 cm.

*Tepal width*.—Medium to broad, 4.0 cm to 7.0 cm.

*Tepal shape*.—Elliptic.

*Tepal, shape in cross-section*.—Concave.

*Tepal, curvature in longitudinal section*.—Flat to moderately reflexed.

*Tepal, reflexing of apex*.—Not applicable.

*Tepal apex*.—Acuminate.

*Tepal base*.—Truncate.

*Tepal, number of colors of upper surface*.—2.

*Tepal, main color of upper surface*.—Closest to RHS 83D (Violet) but slightly paler and more purple.

*Tepal secondary color of upper surface*.—RHS 156D (Greyed-White) tinged with purple.

*Tepal, distribution of secondary color of upper surface*.—Central bar.

*Tepal, main color of lower surface*.—Closest to RHS N79D (Purple) but much paler.

*Tepal, secondary color of lower surface*.—Closest to RHS N79D (Purple) but much paler.

*Tepal, undulation of the margin*.—Absent or very weak.

*Tepal, twisting along longitudinal axis*.—Absent.

*Petaloid staminodes*.—Absent.

Reproductive organs:

*Filament color*.—Light violet, RHS 83D.

*Anther color*.—Violet, RHS 87C.

*Stigma color*.—Purple, RHS 77A.

*Style color*.—Yellow-green, RHS 195A.

Fruit and seed set: None observed.

Disease and pest/insect resistance: None observed.

COMPARISON WITH PARENTAL LINES AND KNOWN VARIETY

'utop013' is distinguished from its parents as described in Table 1:

TABLE 1

Comparison with Parental Lines

| Characteristic | Female parent 'Utopia' | Male parent *C. courtoisii* | 'UTOP013' |
|---|---|---|---|
| Sepals | Pale-pink flowers with a darker margin | White | Light-violet |
| Anther | Dark-purple | Dark-violet | Violet |
| Bud | Dark-green | Light-green | Brown-green with dark line |

'UTOP013' can be compared to the commercial variety 'Venosa Violacea' (unpatented). Differences between the two varieties are described in Table 2:

TABLE 2

Comparison with Similar Variety

| Characteristic | 'UTOP013' | 'Venosa Violacea' |
|---|---|---|
| Flower diameter | Medium to large | Small to medium |
| Sepal shape | Elliptic | Elliptic |
| Time of beginning of flowering | Early to medium flowering, first flowers in May/June | Late |

I claim:

1. A new and distinct variety of *Clematis* plant named 'UTOP013' as illustrated and described herein.

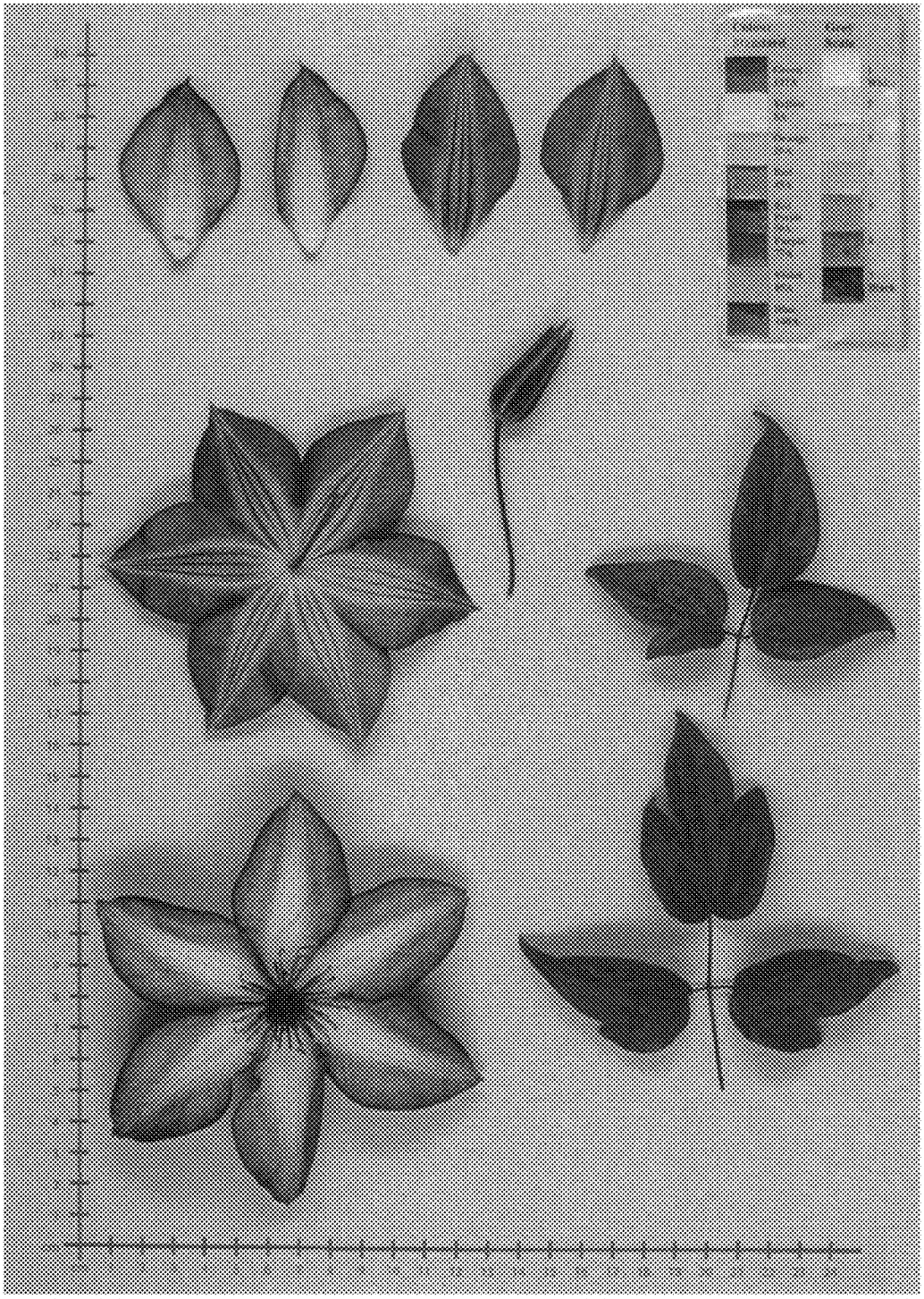

* * * * *